(12) United States Patent
Ezell

(10) Patent No.: US 10,733,578 B2
(45) Date of Patent: Aug. 4, 2020

(54) SYSTEM AND METHOD FOR MANAGEMENT OF RETURN ITEMS

(71) Applicant: Daniel Ezell, Buffalo Grove, IL (US)

(72) Inventor: Daniel Ezell, Buffalo Grove, IL (US)

(73) Assignee: QUALANEX, LLC, Gurnee, IL (US)

( * ) Notice: Subject to any disclaimer, the term of this patent is extended or adjusted under 35 U.S.C. 154(b) by 1056 days.

(21) Appl. No.: 14/312,442

(22) Filed: Jun. 23, 2014

(65) Prior Publication Data

US 2015/0371199 A1 Dec. 24, 2015
US 2017/0011361 A9 Jan. 12, 2017

Related U.S. Application Data

(63) Continuation-in-part of application No. 13/594,540, filed on Aug. 24, 2012, now abandoned.

(51) Int. Cl.
| | |
|---|---|
| *G06Q 10/00* | (2012.01) |
| *G06Q 30/00* | (2012.01) |
| *G07F 7/06* | (2006.01) |
| *A61B 50/36* | (2016.01) |
| *A61B 50/10* | (2016.01) |
| *G06Q 10/08* | (2012.01) |
| *G06Q 50/22* | (2018.01) |

(52) U.S. Cl.
CPC ............ *G06Q 10/30* (2013.01); *A61B 50/10* (2016.02); *A61B 50/36* (2016.02); *G06Q 10/0832* (2013.01); *G06Q 30/01* (2013.01); *G06Q 30/014* (2013.01); *G06Q 50/22* (2013.01); *G07F 7/06* (2013.01); *A61B 2050/105* (2016.02); *Y02W 90/20* (2015.05)

(58) Field of Classification Search
USPC .......................................................... 705/303
See application file for complete search history.

(56) References Cited

U.S. PATENT DOCUMENTS

| | | | |
|---|---|---|---|
| 6,082,519 A * | 7/2000 | Martin ..................... | G07D 9/00 |
| | | | 194/350 |
| 6,611,806 B1 * | 8/2003 | Harvey ................. | G06F 19/322 |
| | | | 705/2 |

(Continued)

OTHER PUBLICATIONS

Final Office Action on U.S. Appl. No. 13/594,540 dated Aug. 12, 2016.

(Continued)

*Primary Examiner* — Maria C Santos-Diaz
*Assistant Examiner* — Lance William White
(74) *Attorney, Agent, or Firm* — Foley & Lardner LLP

(57) ABSTRACT

A method for collecting returned items or information about returned items and evaluating return policy criteria with respect to collected items, and a system for the same, are disclosed. The method includes providing a station, such as a kiosk terminal, preferably at a pharmacy location. The station includes a computer and a user interface including a touch screen interface. Items, for example, pharmaceutical items to be returned are brought to the station. The user enters information at the station, such as by scanning a bar code on a container of the item, weighing the item or its contents, and entering lot number and expiration date associated with the item. A system and method for facilitating recalls is also provided.

22 Claims, 6 Drawing Sheets

(56) References Cited

U.S. PATENT DOCUMENTS

| | | | |
|---|---|---|---|
| 6,754,637 B1* | 6/2004 | Stenz | G06Q 10/0837 |
| | | | 705/26.1 |
| 7,487,100 B2 | 2/2009 | Mallett et al. | |
| 7,620,559 B2 | 11/2009 | Mallett et al. | |
| 7,881,965 B2* | 2/2011 | Bowles | G06Q 10/30 |
| | | | 705/1.1 |
| 8,380,532 B1* | 2/2013 | Zaccaro | G06Q 30/0207 |
| | | | 705/2 |
| 8,573,426 B2* | 11/2013 | Maness | B09B 3/0075 |
| | | | 206/204 |
| 8,635,168 B2* | 1/2014 | Junger | G06Q 10/0833 |
| | | | 705/302 |
| 8,719,048 B1* | 5/2014 | Zaccaro | G06Q 10/30 |
| | | | 705/2 |
| 2001/0037207 A1* | 11/2001 | Dejaeger | G06Q 20/10 |
| | | | 705/39 |
| 2001/0041968 A1* | 11/2001 | Hamilton | A61J 7/02 |
| | | | 702/128 |
| 2002/0019785 A1* | 2/2002 | Whitman | G06Q 10/087 |
| | | | 705/28 |
| 2002/0032582 A1* | 3/2002 | Feeney, Jr. | G06F 19/3462 |
| | | | 705/2 |
| 2002/0087554 A1* | 7/2002 | Seelinger | G06F 19/326 |
| 2003/0093328 A1* | 5/2003 | Koons | G06Q 10/087 |
| | | | 705/26.35 |
| 2004/0204867 A1* | 10/2004 | Smith | G06F 19/327 |
| | | | 702/30 |
| 2005/0096941 A1 | 5/2005 | Tong | |
| 2006/0196926 A1* | 9/2006 | Benson | G07F 17/12 |
| | | | 235/375 |
| 2006/0277110 A1* | 12/2006 | Witter | G06Q 10/10 |
| | | | 705/26.1 |
| 2007/0250339 A1* | 10/2007 | Mallett | B07C 7/005 |
| | | | 705/308 |
| 2007/0292117 A1* | 12/2007 | Saether | G01N 21/8806 |
| | | | 396/20 |
| 2008/0045771 A1* | 2/2008 | Regla | A61L 11/00 |
| | | | 588/301 |
| 2008/0195247 A1* | 8/2008 | Mallett | A61L 11/00 |
| | | | 700/225 |
| 2008/0195416 A1* | 8/2008 | Tribble | G06Q 50/22 |
| | | | 705/2 |
| 2011/0184751 A1* | 7/2011 | Holmes | G06F 19/3462 |
| | | | 705/2 |
| 2011/0259471 A1 | 10/2011 | Maness | |
| 2012/0029980 A1* | 2/2012 | Paz | B07C 5/34 |
| | | | 705/14.1 |
| 2012/0173440 A1* | 7/2012 | Dehlinger | B65F 1/1484 |
| | | | 705/308 |
| 2013/0168300 A1* | 7/2013 | Malone | G07F 7/0609 |
| | | | 209/583 |
| 2014/0330579 A1* | 11/2014 | Cashman | E04H 1/1222 |
| | | | 705/2 |

OTHER PUBLICATIONS

Non-Final Office Action on U.S. Appl. No. 13/594,540 dated Apr. 26, 2016.
Non-Final Office Action on U.S. Appl. No. 13/594,540 dated Jun. 21, 2017.
U.S. Office Action on U.S. Appl. No. 13/594,540 dated Dec. 5, 2017.

* cited by examiner

SYSTEM AND METHOD FOR MANAGEMENT OF RETURN ITEMS

CROSS-REFERENCE TO RELATED APPLICATIONS

This is a continuation-in-part of application Ser. No. 13/594,540, filed Aug. 24, 2012, which is hereby incorporated by reference in its entirety.

BACKGROUND OF THE INVENTION

Field of the Invention

The present invention relates to a system and method for the collection or management of items, and more particularly, to the collection of returnable items such as pharmaceuticals and the accounting and return policy management system with respect thereto.

Background

The pharmaceutical industry in particular requires many return transactions to take place. Pharmaceutical items such as containers of prescription or over-the-counter drugs and medications may be returned by the retail pharmacy to the drug manufacturer for credit under certain circumstances. For example, various manufacturers have specific return policies which will determine to what extent credit will be given for returned pharmaceuticals such as items which are expired, short dated, damaged, defective, or recalled.

Conventionally, the manner in which pharmaceutical items are returned and disposed of is a rather inefficient and costly process. Typically, pharmacies will ship such items to a third party contractor who will record the details of each item including information such as lot numbers, expiration dates, quantities, product numbers, etc. The third party will determine what credits it believes are due under the various return policy rules. Then, the items are typically shipped to a contractor hired by the manufacturer to verify the details of the returned items. These contractors analyze the same information again, and apply the return policies to verify or refute the application of the return policies. The returned items must then be sent through proper disposal channels based on the pertinent regulations, such as controlled substances being sent to an incinerator.

This conventional process is a very inefficient process with the involvement of multiple parties, multiple shipping transactions, and significant costs to both the pharmacies and the manufacturers. Furthermore, regulations relating to the shipping of pharmaceuticals in various categories by agencies such as the EPA and FDA, et al., are placing increasing limitations on the ability of pharmacies to ship various items, and particularly so when such a shipment crosses state lines. This can result in pharmacies failing to claim credits rightfully due to them because they have no suitable method to ship a returned item. In addition, expired and otherwise returnable pharmaceutical items may pile up and take up space at retail locations.

There is no prior art system or method to address these problems. In other industries, such as in the medical waste industry, there are various waste receptacle units which are designed to accept various types of medical waste, including sharps. For example, U.S. Pat. No. 7,620,559 issued to Mallett et al., discloses a medical waste disposal unit which provides for different openings to different containers for different types of waste. However, there is no system in place to enter information which would relate to returning an item, nor is there any determination of return policy compliance. Numerous other similar units exist in the prior art, however, none of them provide for return policy analyses.

U.S. Pat. No. 7,487,100, also issued to Mallet et al., discloses a method of sorting regulated drug waste. But again, there is no method for providing details related to determining whether a return credit is available under a return policy.

U.S. Pat. No. 6,754,637 issued to Stenz discloses a method for managing return processing. Software is used to address return policy issues. Other such systems exist. However, there is no method disclosed to verify the details of the product being returned, and the product must still be shipped for verification.

None of these prior devices provide for an efficient system which verifies the item contents without shipping to another site, and addresses return policy issues without having to ship returned items to an independent contractor for verification. Thus, there continues to be a need for a more efficient method and system for the collection and management of returned items.

SUMMARY

The present invention is a method and system for collecting returned items and determining return policy compliance. This method and system consolidate the collection, verification, and return compliance steps into a much more efficient process. While this method and system may be applied to any suitable industry, one industry in which the method is particularly well-suited is the pharmaceutical industry. It is understood that the following discussion and description relate to certain embodiments of the invention, but that the scope of the invention is broad enough to include collection in other industries as well.

In various different embodiments, the invention includes providing a kiosk type station at a retail location such as a retail pharmacy location or any pharmacy location. Ideally, the station would be located in an area for personnel access only. Employees are able to use the station to deposit pharmaceutical items for return, such as items which are expired, short dated, damaged, defective, or recalled.

In various embodiments, the station includes a cabinet and an interior in which two receptacles are placed. One receptacle is placed in a non-controlled substance area, and the other is in a controlled substance area, as various regulations require these two categories of waste to be treated differently. The receptacles are locked within the station and can be accessed to deposit returned items via access panels which open selectively depending on which category the returned items belong to.

A user enters information to identify the user at the station. Then, various pieces of information are input into the system, either by user interface such as touch screen, or by various station instruments. In various embodiments, the information may include any combination of scanned bar code, product number, lot number, expiration date, weight, pill count, type of packaging and whether sealed or partial package, whether prescription vial, etc. The station may include various cameras to record events for later verification. A pill counting tray and scale are included. Optionally, an automated pill counting sensor is included. Once all information is entered, a panel may open on one side or the other, depending on the category of the item. The user then deposits the item into a chute and it drops into the removable receptacle below. Optionally, the user may place the items, such as pills, back into their original container or a bag, and optionally label the container or bag with a provided label such as a bar coded or other identifying label. Powders or liquids may be handled differently. Once one of the receptacles becomes filled to a predetermined level, the system may notify the user at the station, or notify an off site party such as a waste disposal contractor, that the receptacle requires removal and changing.

Once information is entered, various portions of information can be checked, such as whether the weight and count of the item matches existing database data for the item. The system then checks whether return policy rules allow the item to qualify for a return or partial return. This may be done using updated information at the station itself. However, the preferred method is to enable the system to communicate via a network or the internet with a database server which is maintained with updated information related to pharmaceutical items or other items and manufacturer return policy rules. Once the system determines to what extent the item qualifies for return, and record and accounting is stored and optionally sent to interested parties such as the retail facility, the manufacturer, or a third party contractor.

Thus, this system greatly streamlines the process for obtaining credit for returned items such as pharmaceuticals, and disposing of them. Instead of the items being shipped to a manufacturer or third party contractor, which is sometimes prohibited in view of various local and national government regulations, the verification steps are largely automated and take place right on site at the pharmacy location. Waste is then taken directly to a waste disposal facility such as a waste consolidation facility or an incinerator directly from the pharmacy location. Optionally, waste may be consolidated at another location prior to being taken to the waste disposal facility.

In certain embodiments, the system of the present invention is a station which is adapted to sit atop a table or counter. Such a system may be separate from any receptacle compartments. A table top embodiment of the present invention is particularly useful when space is limited. The table top station includes a computing device and user interface.

In its various embodiments, the table top station enables a user to identify himself or herself. For example, a password or biometric data can be provided to identify the user. The user can then enter information about the item. For example, for a pharmaceutical product, the name of the drug can be entered.

In various embodiments, the user can then select whether the item is being returned, enter a lot number, receive an expiration date generated by the system via use of the data base that corresponds to the lot number, and the system can determine whether the item falls under a particular return policy.

Various alternatives may be provided for the user to input the quantity of the item remaining in the container, such as a manual counting tray or an automatic pill counter. A scale may be provided to enable the user to weigh the product, particularly if the product is a fluid inside a container.

Furthermore, the station is ideally provided with one or more cameras adapted to take photographs or video of the product, of the container, of various portions of the process, or of the user.

Ideally, the station includes a label printer and prints return labels of the product. Identification labels may also be printed. If desired, the station may include bags for containing the product.

Still other objects and advantages of the present invention will become readily apparent to those skilled in the art from the following detailed description, wherein it is shown and described only the preferred embodiments of the invention, simply by way of illustration of the best mode contemplated of carrying out the invention. As will be realized, the invention is capable of other and different embodiments and its several details are capable of modifications in various obvious respects, without departing from the invention. Accordingly, the drawings, wherein like reference numerals represent like features, and description are to be regarded as illustrative in nature and not as restrictive.

DETAILED DESCRIPTION OF THE INVENTION

Figure 1:
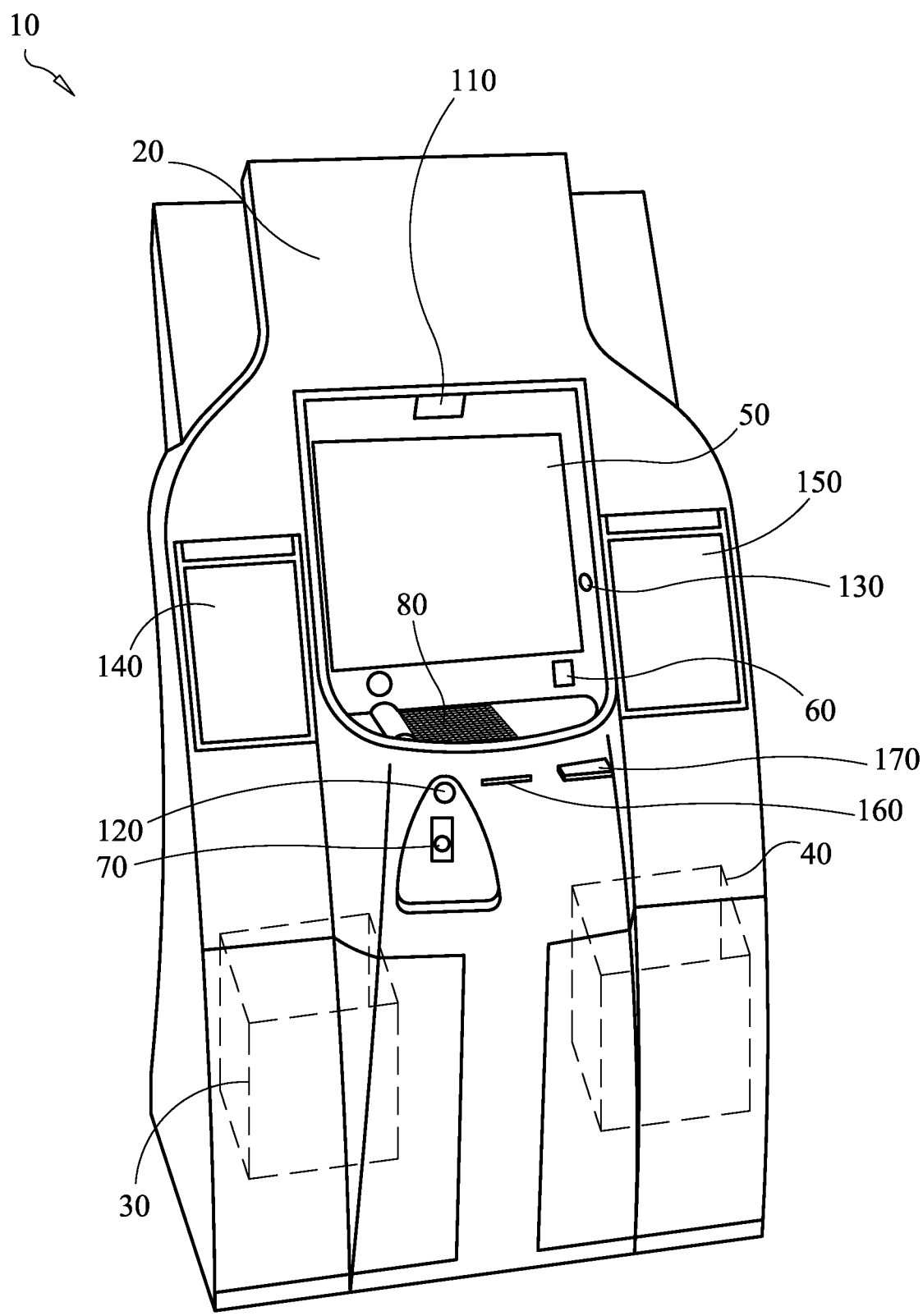
FIG. 1 shows a perspective view of one embodiment of the station of the present invention.
Figure 2:
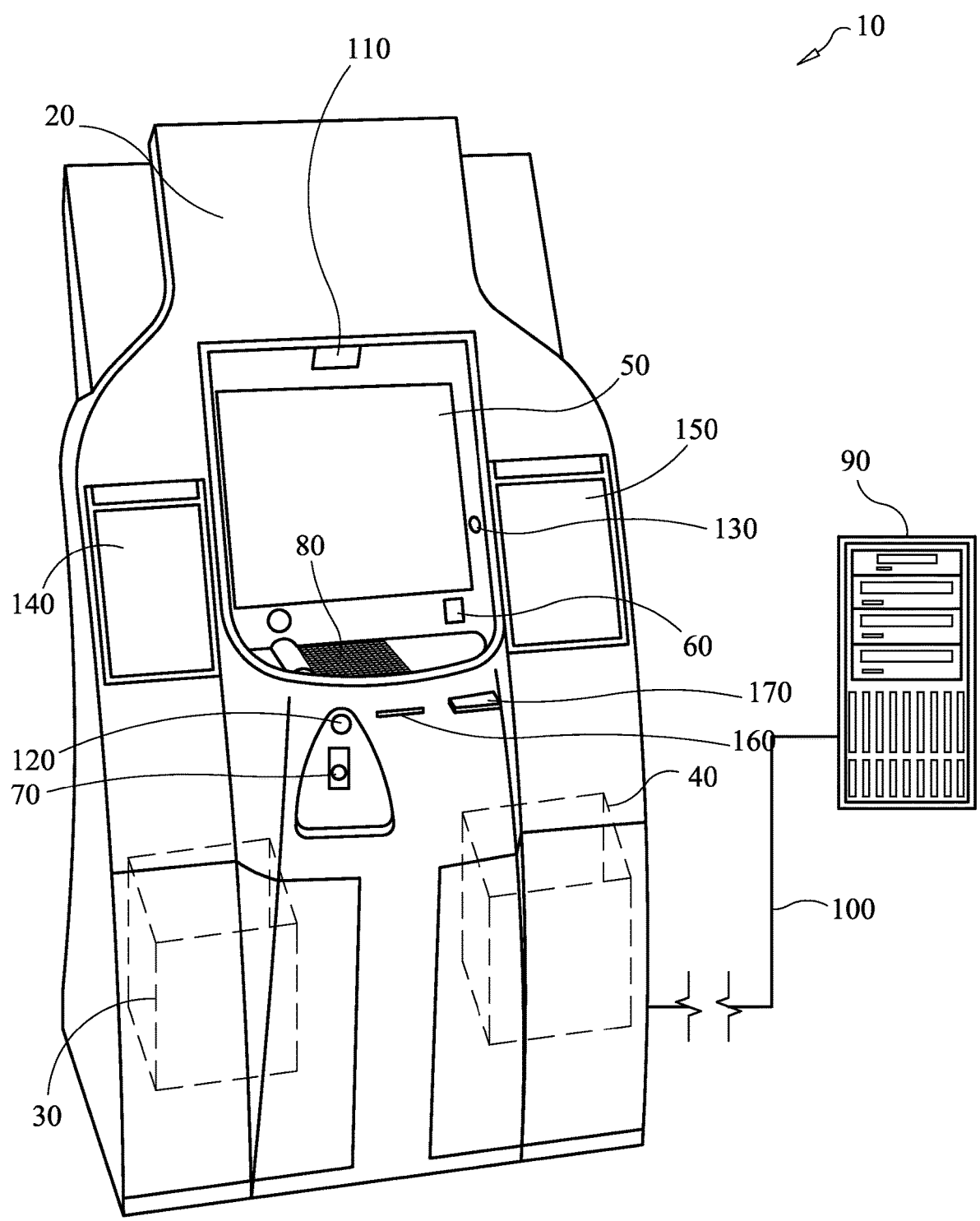
FIG. 2 shows a perspective view of one embodiment of the system of the present invention.
Figure 3:
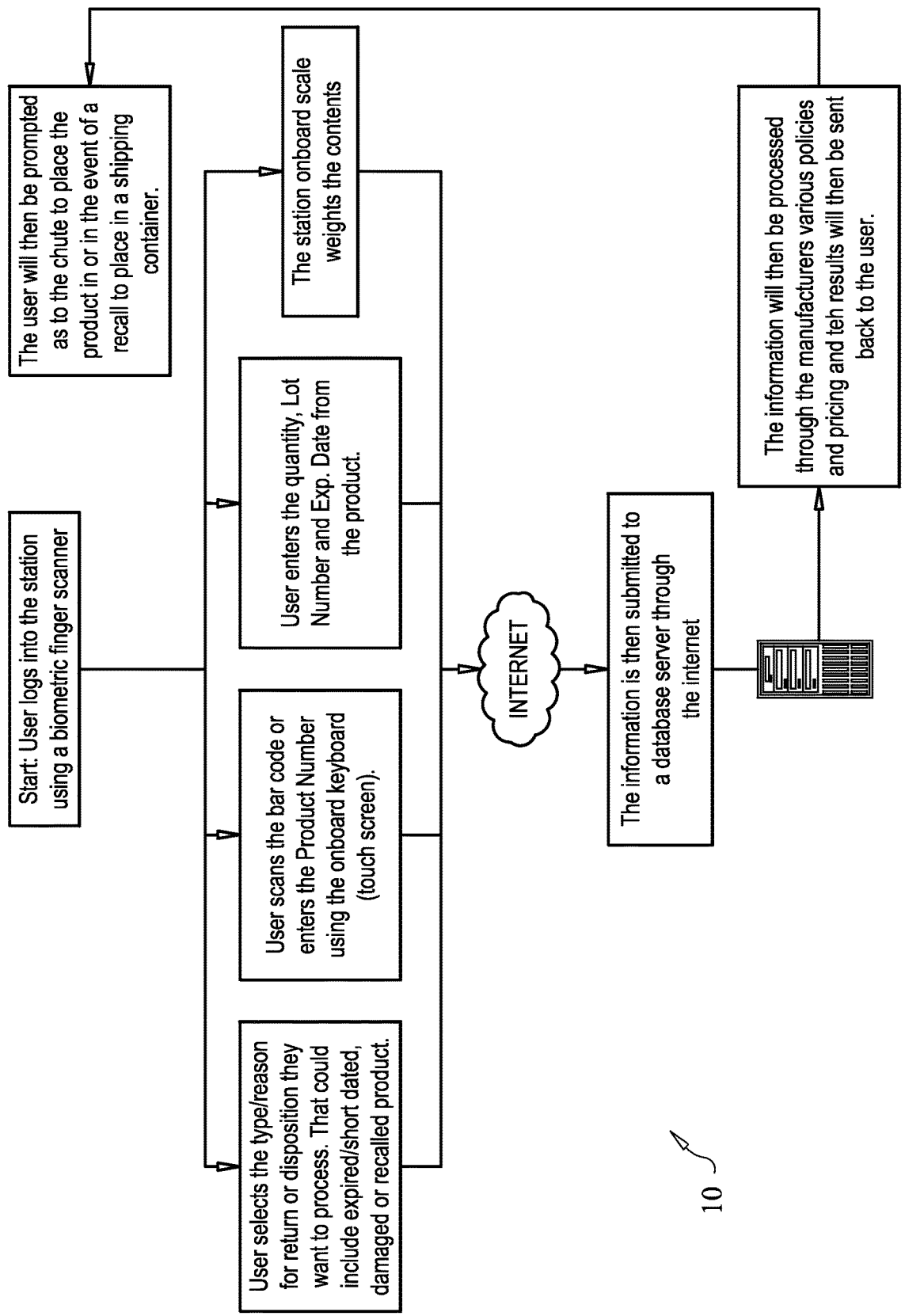
FIG. 3 shows a diagram of one embodiment of the method of the present invention.
Figure 4:
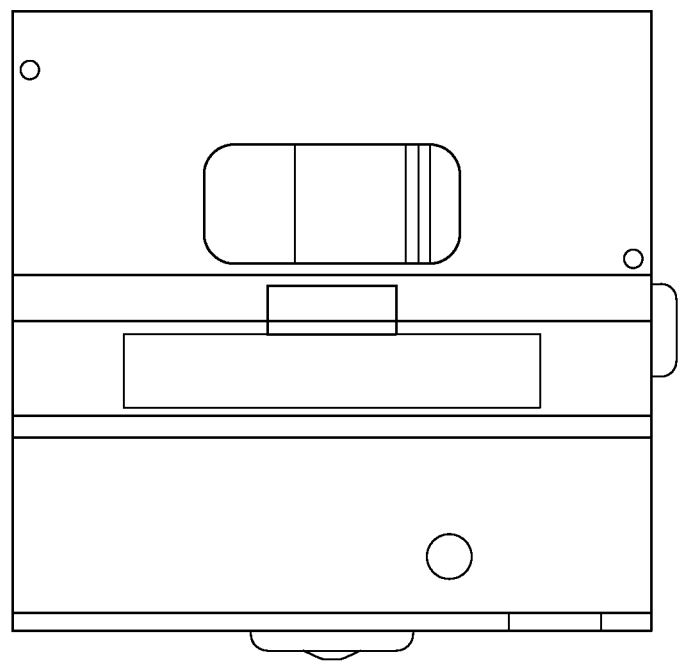
FIG. 4 shows one embodiment of a table top version of the system of the present invention.
Figure 5:
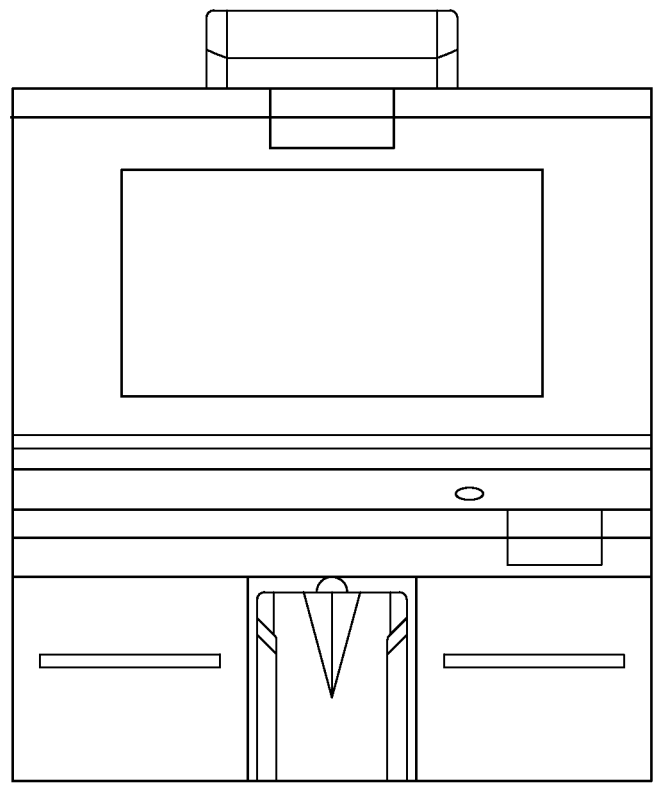
FIG. 5 shows another embodiment of a table top version of the system of the present invention.
Figure 6:
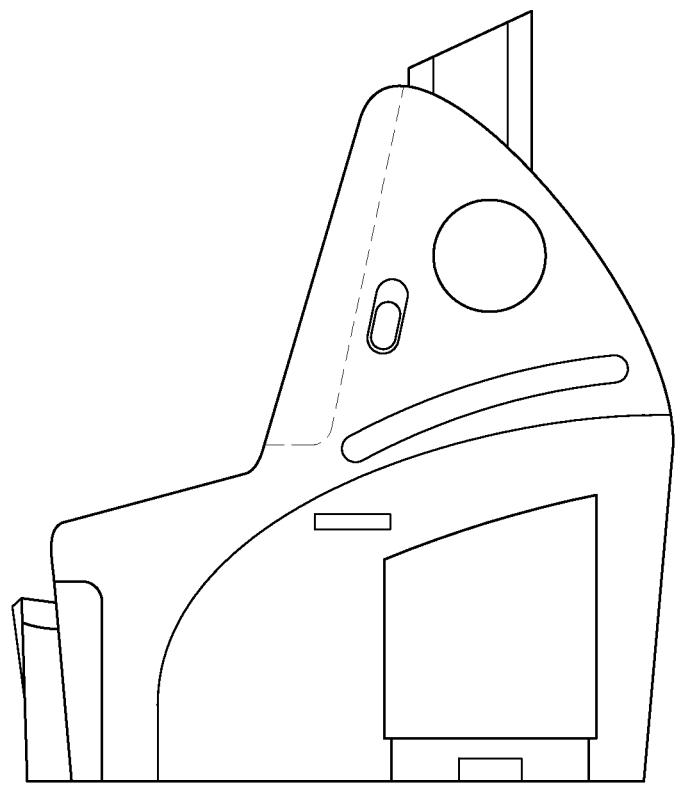
FIG. 6 shows another embodiment of a table top version of the system of the present invention.
Figure 7:
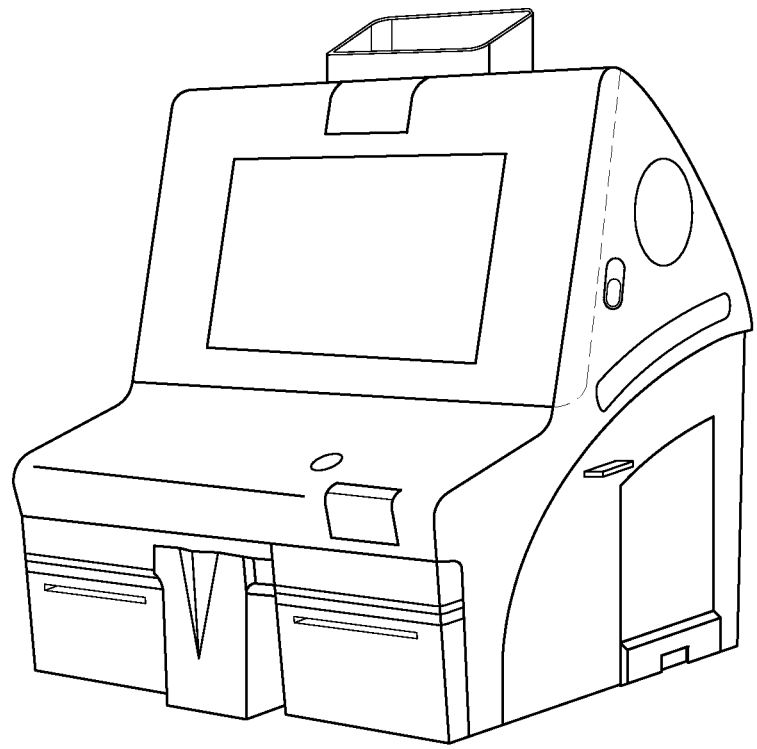
FIG. 7 shows another embodiment of a table top version of the system of the present invention.
Figure 8:
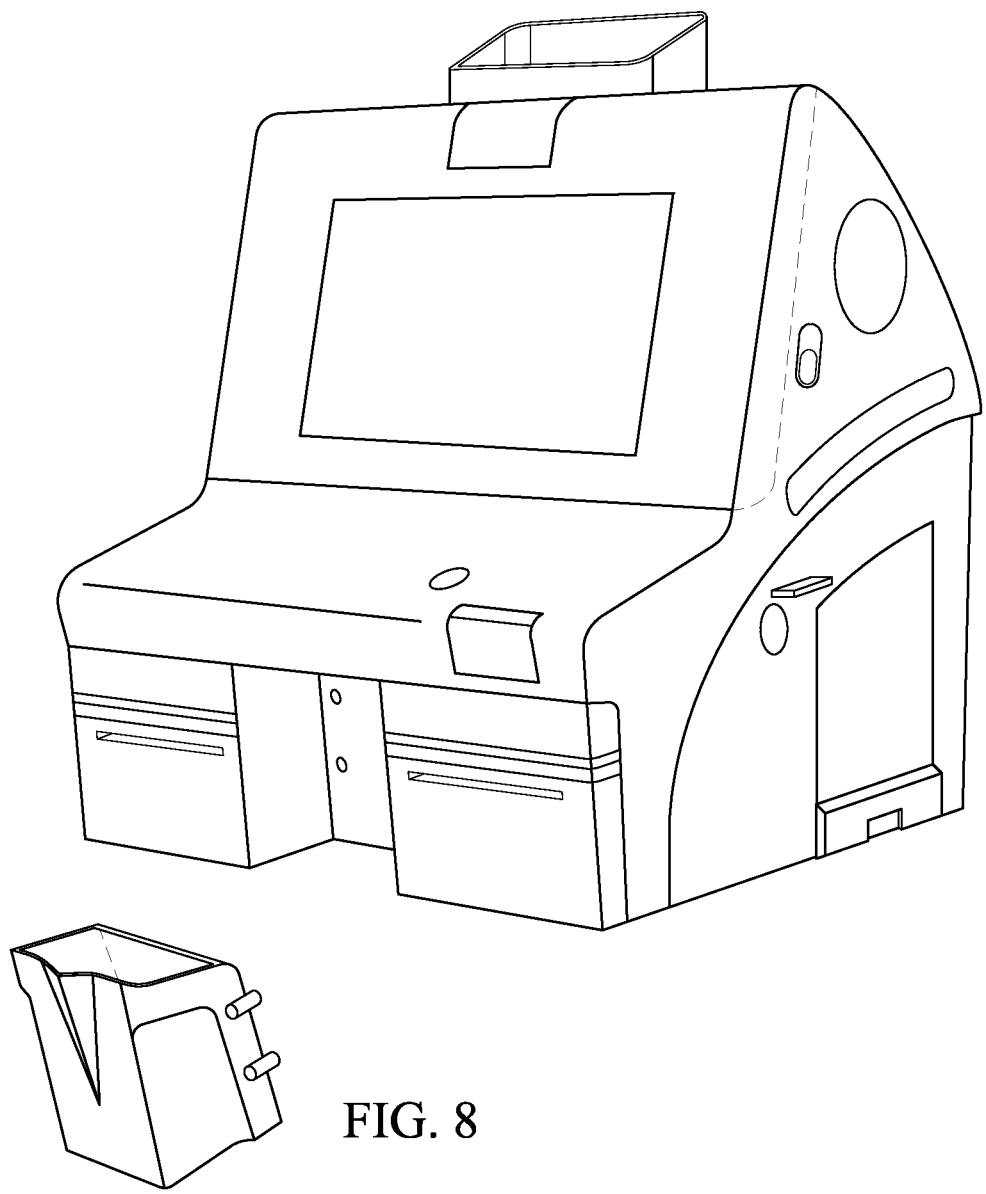
FIG. 8 shows another embodiment of a table top version of the system of the present invention.

While this invention is susceptible of embodiments in many different forms, there are shown in the drawings and will herein be described in detail, preferred embodiments of the invention with the understanding that the present disclosure is to be considered as an exemplification of the principles of the invention and is not intended to limit the broad aspect of the invention to the embodiments illustrated.

The present invention is a method and system 10 for collecting returnable items and determining return policy compliance. The method and system is applicable to many different types of items which can be returned for potential credit. It is understood that this system and method can be adapted or used with respect to any suitable item. However, in a preferred embodiment, the method and system is used in conjunction with pharmaceutical items being returned. Typically, these items include expired drugs, damaged items, short dated drugs meaning drugs with expiration dates approaching within a short time period, defective items, or recalled items.

In various embodiments, the system 10 and method include providing a station 20 having a first receptacle 30 adapted to receive a returnable item. A second receptacle 40 also adapted to receive a returnable item is preferably provided. The receptacles are ideally removable, though they are optionally locked within the station 10. Access to remove them may be provided to authorized persons either identified by the system 10 or having a key or combination. The receptacles may be shippable containers such as shipping boxes, or they may be any other suitable containers.

The station 10 is provided with a computer and a user interface such as a touch screen 50. A user is able to enter information using the touch screen. In certain embodiments, a user initially is identified by the system via any of various methods, such as by scanned ID, biometric finger scanner 60, or user name and password identification. The user then enters information about the item being returned. Such information may include the reason for the return, such as expired, short dated, damaged, defective, recalled, etc. The user may then scan a bar code on the item using a scanner 70 or 170, or enters a product number associated with the item. Further information is preferably entered, such as a lot number associated with the pharmaceutical item and an expiration date.

In various embodiments, the user is then prompted to empty the contents of the container of the item onto a pill counting tray 80, count the contents, whether pills, tablets, capsules, etc., and then replace them into the container. The tray 80 is preferably the top surface of a scale which weighs the item or its contents. Optionally, and automatic pill counting sensor is included. The quantity information, as well as the weight, are input into the system. Various verifications are preferably performed by the system, such as verifying that the weight of the item matches its type and quantity based on known information stored in a database related to the item.

The information is then evaluated with respect to return policy rules. The rules may be updated in a database at the station 20 itself, or a database server 90 may be networked with the station 20 via a network or internet connection 100. The information provided is checked against return policy rules to determine whether the return qualifies for credit. The manufacturer or its agent (or an independent contractor or third party) can be sent a report of this determination and an accounting is kept. Preferably, the station is located at a pharmacy location, and the pharmacy company can also have a report of the analysis and an accounting sent.

In various embodiments, a first camera 110 records at least a portion of the user's transaction at the station for possible subsequent verification. A second camera 120 and optionally a third camera 130 are preferably placed in locations to record various views of the item being returned for verification. Records from the cameras may be viewed or spot checked at subsequent times to verify the user's actions.

A first access panel 140 and second access panel 150 are preferably provided. These panels are opened and closed by the system based on whether the item is determined to fit into one category or another. In the embodiment of returning pharmaceutical items, the item is determined by the system using information input by the user whether the item is a controlled or non-controlled substance. If it is a controlled substance, the second access panel 150 may open to allow the user to deposit the item into the second receptacle 40. If the item is a non-controlled substance, the first access panel 140 may be opened to allow the user to deposit the item into the first receptacle 30.

In certain embodiments, the station 20 may further include a label printer 160 for printing labels, such as for shipping a box for a recalled item. In the event an item is recalled, the system may be used to display this information on the screen. Thus, if a pharmacy location is sent a recall notice via this station, the station may require the user to act on the recall before authorizing further use.

As the system provides a verification and accounting of the items deposited, and to what extent return policies should be implemented, no further third party contractor or manufacturer need verify the contents of the receptacles. Thus, the receptacles can be transported to a waste disposal facility such as a dump or incinerator. Access is provided to authorized parties to remove the receptacles and transport them.

The system and method of the present invention is particularly advantageous in the event that a product is recalled. This is particularly relevant with respect to the pharmaceutical industry. Conventionally, when a recall is issued in the pharmaceutical industry, numerous steps must be followed. A notification letter and response card are printed, typically by the manufacturer or its agent, notification kits must be mailed or shipped to retailers, response cards must be completed by the retailers and returned to the manufacturer or manufacturer's agent via mail or courier. Once the response cards are received by the manufacturer or its agent, the information must be manually entered into a recall reporting system. A shipping label must then be printed by the manufacturer or its agent and shipped to the retailer if the retailer has product subject to the recall, and the retailer then must ship the product to a return center. Recall reports are then provided to the FDA, and eventually the returned product is disposed of.

As will be seen, in the various embodiments of the present invention are a great improvement to such a conventional method. In the present invention, notification letters and response cards can be electronically transmitted directly to the station of the retailer. The response cards can be completed electronically and sent electronically to the manufacturer or its agent. The station can then, optionally, generate a shipping label which can also be printed at the station. This label can be used immediately by the retailer to ship the product to a return center. Once the recall is approved, the product is disposed of. Thus, a great deal of time and shipping expense can be saved, and manual entry of data can be done electronically. The retailer is able to enter the data related to the product at the station in the same fashion as returns are entered.

In various embodiments, the system of the present invention is a table top version of the system. In certain embodiments, the table top version may be separate from any receptacles. In such a version, the system includes a station, preferably adapted to sit atop a table or counter. Such an embodiment is particularly useful when the available space for the system is limited.

The station includes a method for identifying an individual user, such as via a password, or a biometric data input mechanism such as a fingerprint scanner. The station includes a computing device and a user interface, and software running on the computing device. The user interface enables the user to enter at least a first piece of information associated with an item to be returned. The information may be identifying information, such as a barcode. A keyboard or a barcode scanner may be used.

The station has access to a database which can be maintained, such as a local database or a database linked to the station via a network. Once the item has been identified, return policy information associated with the item can be determined. The user can enter additional information, such as a lot number. The lot number can be used to determine an expiration date of the item, such as a pharmaceutical drug, or the expiration date may be entered by the user. Once the expiration date is determined, return policy information associated with the item can be determined from the information contained in the database, and it can be determined whether the item can be returned for a refund or partial refund. It is understood that the manner in which information is processed can be configured in a number of different ways. For example, the station may include software which allows information to be input and then transferred to a server having access to a database for further processing. Alternatively, the processing of the information and accessing of the database can be enabled at the station itself.

Once a product identifier is entered, the system may allow the user to select a packaging method, such as a bottle, box, particular size, etc. The user may be given the opportunity to input whether the container is sealed or unsealed. The station ideally includes a mechanism to enable the user to count items within the packaging, such as pills or capsules.

In certain embodiments, the station includes a manual counting tray. In others, the station includes an automatic pill counter. In addition, the station may include a scale. The scale can be particularly useful in measuring the weight of containers containing a liquid product. In certain preferred embodiments, the scale may be a pull out, retractable scale on the station.

In various table top embodiments, one or more cameras may be included to photograph, take video footage, or both, with respect to various portions of the process. The item may be photographed or video recorded during the weighing process, during the counting process, or during other portions of the process. The cameras may also take images of the user for verifying identity upon viewing.

In certain preferred table top embodiments, the station also includes at least one label printer. The station may generate and print a shipping label for a return item. An identification label may also be printed.

As the system is ideally networked, notices may be sent to the station from a remote location. For example, a recall notice may be sent to the station. The user may then identify himself or herself, and take action with respect to a recall in a similar fashion to the process for a return.

The table top system may optionally be linked to a receptacle station. The table top station can then provide instructions with respect to which receptacle should be used. Optionally, a signal can be sent to the receptacle station to open one or another receptable.

In various embodiments, the evaluation of the return policy compliance may occur at a server level. For example, the process may include the step of providing a networked station having a computing device and a user interface adapted to enable a user to enter information related to a returnable item, receiving the information related to the returnable item at said station, enabling the information to be transmitted from the station to a server, evaluating at least a portion of that information with respect to a return policy associated with the returnable item, and determining whether or to what extent the item complies with the return policy.

In such embodiments, the evaluation process may be implemented at the server level, and the may employ the use of a database having the return policy information needed to evaluate the compliance of the return and whether and in what amount a refund or credit may be due. Multiple evaluations may occur as batched processes. The timing of the batch process may be set at predetermined intervals, or may follow other timing specifications.

In certain embodiments, this process may be implemented as follows. The servers may have access to a central database and file servers. The batch program run by each server may process credit or debit memos and returns. The returns can be aggregated by the retailers involved and bundled together for a single transaction. They are archived and transmitted to the servers, and the servers can run a batch program to evaluate multiple returns during one evaluating step. Various databases technologies and transmission protocols can be used, as will be clear to one of ordinary skill in the art.

In various embodiments, item returns are evaluated locally at the station, and the information is stored locally. Then, the station may transmit that information to a server. In certain embodiments, the batch programs may function as follows, although any suitable procedure with respect to batch programs is contemplated to be within the scope of the present invention. The servers may have a batch program installed thereon and may process one or multiple manufacturers related to the returns. The batch programs may run at frequent predefined intervals, or at any intervals desired. Alternatively, other parameters may be set to determine when the batch program will run, such as based on the number of claims. The batch program, when run, processes the return items which are on the manufacturer's schedule. Credit and debit memos are processed at various intervals, such as each hour, for example. Custom or standard return formats may be used for each manufacturer. Each manufacturer may send credit or debit memos for reconciliation with respect to each return item. In the event returns for multiple retailers are being processed, each retailer may have an ID, and the returns are batched using those IDs. Each manufacturer may have a time window for accepting returns, such as a set time each day or each weekday. The returns are recorded in a central database and may be reviewed. Preferably, the transmissions take place using a secure channel or protocol. Optionally, encryption may be used, and signatures can be used. It is understood that the servers can communicate with stations for updates, notifications, and return items.

While specific embodiments have been illustrated and described, numerous modifications come to mind without significantly departing from the spirit of the invention and the scope of protection is limited by the scope of the accompanying claims.

What is claimed is:

1. A method comprising:
   receiving, by a computer user interface device of a kiosk station, product information associated with a packaged item at the kiosk station, wherein the packaged item contains a pharmaceutical product, and wherein the product information comprises an indication that the pharmaceutical product is to be returned;
   forming, via a special-purpose computer, a return determination based on whether the pharmaceutical product qualifies for a credit using return policy information and the product information, wherein the return policy information comprises database data on credit criteria for the pharmaceutical product;
   obtaining verification information of the pharmaceutical product in accordance with the return policy information and the product information, wherein the obtaining of verification information of the pharmaceutical product comprises:
      capturing an image of the packaged item via a camera at the kiosk station; and
      weighing, via a scale at the kiosk station, the packaged item to obtain a weight of the packaged item and the pharmaceutical product, wherein a surface of the scale is within a field-of-view of the camera;
   transmitting, to the pharmaceutical manufacturer, the verification information, wherein the verification information comprises the image and the weight;
   providing credit information for the pharmaceutical product upon the return determination and the obtained verification information;

upon provision of the credit information, categorizing, via the special purpose computer, the pharmaceutical product based on the product information, wherein the categorizing includes at least one of determining that the pharmaceutical product of the packaged item belongs to a first category and determining that the pharmaceutical product of the packaged item belongs to a second category;

opening a first disposal channel in response to determining that the pharmaceutical product of the packaged item belongs to the first category, wherein the first disposal channel leads to a first container; and opening a second disposal channel in response to determining that the pharmaceutical product of the packaged item belongs to the second category, wherein the second disposal channel leads to a second container, wherein the first container is spatially separated from the second container.

2. The method according to claim 1, further comprising:
providing a networked connection between a database server having policy parameters and the special-purpose computer, wherein the database server is configured to receive the information from the computer over said networked connection.

3. The method according to claim 2, further comprising:
determining an item category based on at least a portion of the product information.

4. The method according to claim 3, wherein the item category is either a non-controlled pharmaceutical substance or a controlled pharmaceutical substance.

5. The method according to claim 4, wherein providing credit information for the pharmaceutical product upon the return determination and the obtained verification information comprises printing an identification number for association with the pharmaceutical product.

6. The method according to claim 5, wherein a portion of the product information is an indication of a reason for returning the item.

7. The method according to claim 6, wherein a portion of the product information includes a product number or bar code data.

8. The method according to claim 7, wherein the pharmaceutical product comprises pharmaceutical pills, and wherein a portion of the product information includes a quantity of pharmaceutical pills.

9. The method according to claim 8, wherein a portion of the product information includes an expiration date of the pharmaceutical product.

10. The method according to claim 9, wherein a portion of the product information includes a lot number associated with the pharmaceutical product.

11. The method according to claim 1, further comprising providing disposal instructions for the pharmaceutical product.

12. The method according to claim 1, wherein the pharmaceutical product comprises pharmaceutical pills, and wherein the pharmaceutical pills comprise at least one of tablets or capsules.

13. The method according to claim 1, wherein the first category is that the pharmaceutical product is a controlled substance and the second category is that the pharmaceutical product is an uncontrolled substance.

14. The method according to claim 1, wherein the product information comprises a received weight of the packaged item and the pharmaceutical product, and wherein the verification information of the pharmaceutical product comprises comparing the received weight with the weight of the packaged item and the pharmaceutical product received from the scale.

15. A collection station comprising:
a camera configured to record a packaged item containing a pharmaceutical product;
a scale configured to weigh the packaged item, wherein a surface of the scale is in a field of view of the camera;
a first disposal channel providing access to a first container;
a second disposal channel providing access to a second container, wherein the second container is spatially separated from the first container;
a special-purpose computer and a user interface, wherein the special-purpose computer is configured to:
receive product information associated with the packaged item containing the pharmaceutical product via a user interface, wherein the product information comprises an indication that the pharmaceutical product is to be returned;
form a return determination based on whether the pharmaceutical product qualifies for a credit using return policy information and the product information, wherein the return policy information comprises database data on credit criteria for the pharmaceutical product;
obtain verification information of the pharmaceutical product in accordance with the return policy information and the product information, wherein the obtaining verification information of the pharmaceutical product comprises weighing via the scale the packaged item to obtain a weight of the packaged item and the pharmaceutical product and capturing via the camera an image of the packaged item;
transmit, to a pharmaceutical manufacturer, the verification information, wherein the verification information comprises the weight and the image; and
provide credit information for the pharmaceutical product upon the return determination and the obtained verification information;
upon providing the credit information, categorize the pharmaceutical product based on the product information, wherein the categorizing includes at least one of determining that the pharmaceutical product of the packaged item belongs to a first category and determining that the pharmaceutical product of the packaged item belongs to a second category;
open the first disposal channel in response to determining that the pharmaceutical product of the packaged item belongs to the first category;
open a second disposal channel in response to determining that the pharmaceutical product of the packaged item belongs to the second category, and
a networked connection between the special-purpose computer and an off-site database server configured to receive information from the special-purpose computer and evaluate the information in view of return policy compliance rules.

16. The collection station according to claim 15, wherein the scale is adapted to provide output weight information to the special-purpose computer.

17. The collection station according to claim 16, wherein the pharmaceutical product comprises pharmaceutical pills, and wherein the scale includes a pill counting tray adapted to allow a user to place and count the pharmaceutical pills.

18. The collection station according to claim 17, wherein the user interface comprises a touch screen interface, and further comprising a scanner adapted to scan a bar code on the packaged item containing the pharmaceutical product.

19. The collection station according to claim 15, wherein said using the camera at the collection station to record the packaged item comprises using the camera at the collection station to record the pharmaceutical product when the pharmaceutical item is distributed in the pill counting tray.

20. The collection station according to claim 15, wherein the camera is a top view camera providing a top view of the surface, further comprising a side view camera, wherein, when the packaged item is placed on the surface, the side view camera provides a side view of the packaged item.

21. A system for collecting items comprising:
a station having a special-purpose computing device having a user interface adapted to enable a user to enter product information associated with a packaged item, wherein the packaged item contains a pharmaceutical product, and wherein the product information comprises an indication that the pharmaceutical product is to be returned;
a camera configured to record the packaged item;
a scale configured to weigh the packaged item and the pharmaceutical product, wherein a surface of the scale is in a field of view of the camera;
a first disposal channel providing access to a first container;
a second disposal channel providing access to a second container, wherein the second container is spatially separated from the first container;
a database containing return policy information related to the pharmaceutical product, wherein the special-purpose computing device is configured to:
receive product information associated with the packaged item containing the pharmaceutical product via a user interface;
form a return determination based on whether the pharmaceutical product qualifies for a credit using the return policy information and the product information, wherein the return policy information comprises database data on credit criteria for the pharmaceutical product;
obtain verification information of the pharmaceutical product in accordance with the return policy information and the product information, wherein the obtaining verification information of the pharmaceutical product comprises weighing via the scale the packaged item to obtain a weight of the packaged item and the pharmaceutical product and capturing via the camera an image of the packaged item;
transmit, to the pharmaceutical manufacturer, the verification information, wherein the verification information comprises the weight and the image; and
provide credit information for the pharmaceutical product upon the return determination and the obtained verification information;
upon providing the credit information, categorize the pharmaceutical product based on the product information, wherein the categorizing includes at least one of determining that the pharmaceutical product belongs to a first category and determining that the pharmaceutical product belongs to a second category;
open the first disposal channel in response to determining that the pharmaceutical product of the packaged item belongs to the first category; and
open a second disposal channel in response to determining that the pharmaceutical product of the packaged item belongs to the second category.

22. The method of claim 1, wherein the categorizing includes at least one of determining based on the verification information that the pharmaceutical product of the packaged item belongs to the first category and determining based on the verification information that the pharmaceutical product of the packaged item belongs to the second category.

\* \* \* \* \*